(12) United States Patent
Lewis et al.

(10) Patent No.: US 9,939,362 B2
(45) Date of Patent: Apr. 10, 2018

(54) HETEROGENEOUS FLUID SAMPLE CHARACTERIZATION

(71) Applicant: MALVERN INSTRUMENTS LIMITED, Malvern Worcestershire (GB)

(72) Inventors: E. Neil Lewis, Olney, MD (US); John McCaffrey, Columbia, MD (US); Vishal Patil, Columbia, MD (US); Kenneth Haber, Brookeville, MD (US)

(73) Assignee: Malvern Instruments Limited, Malvern (GB)

( * ) Notice: Subject to any disclaimer, the term of this patent is extended or adjusted under 35 U.S.C. 154(b) by 0 days.

(21) Appl. No.: 15/120,513

(22) PCT Filed: Feb. 20, 2015

(86) PCT No.: PCT/GB2015/050496
§ 371 (c)(1),
(2) Date: Aug. 19, 2016

(87) PCT Pub. No.: WO2015/124942
PCT Pub. Date: Aug. 27, 2015

(65) Prior Publication Data
US 2016/0356696 A1 Dec. 8, 2016

Related U.S. Application Data

(60) Provisional application No. 61/942,027, filed on Feb. 20, 2014, provisional application No. 62/035,111, filed on Aug. 8, 2014.

(51) Int. Cl.
*G01N 1/00* (2006.01)
*G01N 15/14* (2006.01)
(Continued)

(52) U.S. Cl.
CPC ....... *G01N 15/1459* (2013.01); *B07C 5/3425* (2013.01); *G01N 15/1404* (2013.01);
(Continued)

(58) Field of Classification Search
CPC ....... G01N 2015/1006; G01N 15/1404; G01N 15/1459; G01N 2015/149; G01N 15/1484;
(Continued)

(56) References Cited

U.S. PATENT DOCUMENTS 6,309,886 B1 * 10/2001 Ambrose ........... G01N 21/6456
356/72
8,933,395 B2 * 1/2015 Mueth .................... G02B 21/32
210/732

(Continued)

FOREIGN PATENT DOCUMENTS

WO    WO 2013190326    * 12/2013

*Primary Examiner* — Michael P Stafira
(74) *Attorney, Agent, or Firm* — Kristofer E. Elbing (57) ABSTRACT

The invention relates to methods and apparatus for detecting properties of heterogeneous samples, including detecting properties of particles or fluid droplets in industrial processes. Embodiments disclosed include a particle characterization method, comprising: providing a fluid containing suspended particles; causing at least a first subset of the suspended particles to flow past a first two-dimensional array detector (24); illuminating the first subset of suspended particles as they flow past the first two-dimensional array detector (24) in the fluid; acquiring a plurality of images of the first subset of particles as they flow past the first two-dimensional array detector (24) in the fluid; and automatically counting the particles in the images.

18 Claims, 8 Drawing Sheets

(51) Int. Cl.
*B07C 5/342* (2006.01)
*G01N 15/10* (2006.01)
*G01N 15/00* (2006.01)

(52) U.S. Cl.
CPC ..... *G01N 15/1436* (2013.01); *G01N 15/1463* (2013.01); *G01N 15/1484* (2013.01); *G01N 2015/0038* (2013.01); *G01N 2015/0065* (2013.01); *G01N 2015/1006* (2013.01); *G01N 2015/1043* (2013.01); *G01N 2015/149* (2013.01); *G01N 2015/1409* (2013.01); *G01N 2015/1413* (2013.01); *G01N 2015/1415* (2013.01); *G01N 2015/1465* (2013.01); *G01N 2015/1486* (2013.01); *G01N 2015/1488* (2013.01); *G01N 2015/1493* (2013.01); *G01N 2015/1497* (2013.01)

(58) Field of Classification Search
CPC ....... G01N 15/1434; G01N 2015/0065; G01N 15/1463; G01N 2015/1413; G01N 2015/1409; G01N 2015/1081; G01N 21/6486
See application file for complete search history.

(56) References Cited

U.S. PATENT DOCUMENTS

| | | | | |
|---|---|---|---|---|
| 2002/0031783 A1* | 3/2002 | Empedocles | ......... | B01L 3/5025 435/7.1 |
| 2006/0170912 A1* | 8/2006 | Mueth | ................ | G01N 15/1404 356/244 |
| 2008/0100840 A1* | 5/2008 | Oma | ................... | G01N 15/1463 356/339 |
| 2009/0042310 A1* | 2/2009 | Ward | ................. | G01N 15/1404 436/154 |
| 2013/0038878 A1* | 2/2013 | Muraki | .............. | G01N 15/1459 356/436 |
| 2014/0339446 A1* | 11/2014 | Yamamoto | ......... | G01N 15/1429 250/576 |
| 2016/0109372 A1* | 4/2016 | Wanders | ............ | G01N 15/1404 356/40 |

\* cited by examiner

HETEROGENEOUS FLUID SAMPLE CHARACTERIZATION

FIELD OF THE INVENTION

This invention relates to methods and apparatus for detecting properties of heterogeneous fluid samples, including detecting properties of particles or fluid droplets in industrial processes.

BACKGROUND OF THE INVENTION

Lensless microfluidic detection techniques have been proposed to acquire microscopic images of samples such as biological materials and cells. They operate by acquiring images of suspended samples in close proximity to a high-resolution imaging detector. Their small size has resulted in their use being proposed in a variety of life science applications, including microscopes, smart petri dishes, and point-of-care diagnostic systems.

SUMMARY OF THE INVENTION

In one general aspect, the invention features a particle characterization method that includes providing a fluid containing suspended particles and causing at least a first subset of the suspended particles to flow past a first two-dimensional array detector. Providing the fluid containing suspended particles may comprise suspending particles in a fluid. The first subset of suspended particles are illuminated and a plurality of images of the first subset of particles are acquired as they flow past the first two-dimensional array detector in the fluid. The particles in these images are automatically counted.

In preferred embodiments the step of counting can maintain counts of different types of particles. The step of counting can maintain counts of differently sized particles. The method can further include the step of measuring a position of the particles along an axis normal to the two-dimensional array detector as they flow past the two-dimensional array detector in the fluid. The step of illuminating can illuminate the particles with differently colored light from differently colored sources, wherein the step of acquiring images acquires color images through a Bayer filter having wavelength characteristics that correspond to wavelength characteristics of the sources, with the step of measuring the position of particles operating by detecting the position of the particles relative to the differently colored sources in the colored images. The step of measuring the position of particles can operate by apparent size for particles of known size. The step of causing the particles to flow can cause the particles to flow in a fully developed fluid flow. The step of counting can track particles from frame to frame along lines of flow exhibiting different velocities in the fully developed fluid flow. The step of counting can track particles from frame to frame. The step of counting can track particles from frame to frame by their positions. The step of counting can track particles from frame to frame by their morphological characteristics. The method can further include the step of deriving statistical information about the counted particles. The step of causing suspended particles to flow can cause a laminar flow. The method can be performed independent of any lens.

In another general aspect, the invention features a particle characterization method that includes providing a fluid containing suspended particles, causing at least a first subset of the suspended particles to flow past a first two-dimensional array detector, and causing a sheath flow to flow adjacent the flow caused by the step of causing the suspended particles to flow, to direct the flow of suspended particles toward the two-dimensional array detector. Providing the fluid containing suspended particles may comprise suspending particles in a fluid. The first subset of suspended particles are illuminated and a plurality of images of the first subset of particles are acquired as they flow past the first two-dimensional array detector in the fluid.

In preferred embodiments the steps of causing flow can cause a laminar flow. The method can further include the step of recovering the suspended particles in a higher concentration by splitting an elution resulting from a combination of the particle flow and the sheath flow. The method can be performed independent of any lens. The method can further include the step of reversing both the particle flow and the sheath flow to recover the particles. The method can further include the step of adjusting a ratio between a rate of flow of the particle flow and a rate of flow of the sheath flow. The steps of causing a suspended particle sample flow and a sheath flow to flow can be performed through a channel that is about 100 μm deep with the step of acquiring a plurality of images of the first subset of particles being capable of resolving different particle sizes below about 10 μm.

In a further general aspect, the invention features a particle characterization method that includes providing a fluid containing suspended particles, causing at least a first subset of the suspended particles to flow through a conduit, and causing a sheath flow to flow adjacent the flow caused by the step of causing the suspended particles to flow. Providing the fluid containing suspended particles may comprise suspending particles in a fluid. A portion of the flow that includes a subset of the particles in a first size range is separated out, while at least some of the particles in a second size range are excluded. The separated portion of the flow is provided to a particle characterization instrument, and the particles in the first size range are characterized in the particle characterization instrument.

In preferred embodiments, the step of characterizing can be performed by a DLS instrument. The step of characterizing can be performed by an RMM instrument. the step of characterizing can be performed by an NTA instrument. The steps of causing flow can cause a laminar flow. The step of recovering can be performed by splitting an elution resulting from a combination of the particle flow and the sheath flow. The method can further include the step of acquiring images of the flow while it is adjacent the sheath flow but before the step of separating. The method can be performed independent of any lens. The method can further include the step of counting particles in the images. The step of separating can separate with the first size range covering smaller particle sizes than the second size range. The method can further include the step of reversing both the particle flow and the sheath flow to recover the particles. The method can further include the step of adjusting a ratio between a rate of flow of the particle flow and a rate of flow of the sheath flow.

In another general aspect, the invention features a particle characterization method that includes providing a fluid containing suspended particles, causing the suspended particles to flow past a first two-dimensional array detector, illuminating the suspended particles as they flow past the first two-dimensional array detector in the fluid, and acquiring a plurality of images of the particles as they flow past the first two-dimensional array detector in the fluid. Providing the fluid containing suspended particles may comprise suspending particles in a fluid. Characteristics of individual particles are detected from the images, one or more of the particles are selectively diverted to a first particle characterization instrument based on the detected characteristics of the diverted particles, and the diverted particles are characterized in the first particle characterization instrument.

In preferred embodiments, the step of selectively diverting can be performed by a switching valve. The method can further include at least one further step of selectively diverting one or more further particles to one or more further particle characterization instruments based on detected characteristics of the further diverted particles and characterizing the further diverted particles in the further particle characterization instruments.

In a further general aspect, the invention features a particle characterization instrument, comprising: a hydraulic detection channel having first and second opposing faces; a lensless two-dimensional array detector provided along the first face of the hydraulic detection channel and having a field of view across the hydraulic detection channel; a sample fluid channel 32 opening into the hydraulic detection channel and positioned to direct a sample flow across the first face of the hydraulic detection channel within the field of view of the array detector; a sheath fluid channel 34 opening into the hydraulic detection channel and positioned to direct a sheath flow adjacent the sample flow across the second face of the hydraulic detection channel; and an illumination source positioned to illuminate the sample flow within the field of view of the array detector.

The hydraulic detection channel may have a width in a direction normal to the plane of the detector of between 50 and 150 µm, optionally between 80 and 120 µm and further optionally around 100 µm. The width of the hydraulic detection channel may allow the instrument to detect and count particles smaller than 10 µm, and optionally greater than 1 µm or 0.5 µm.

The instrument may further include a sample flow driver 36 hydraulically connected to the sample flow channel, a sheath flow driver 38 hydraulically connected to the sheath flow channel, and means for adjusting a ratio between a flow rate of the sample flow driver and a flow rate of the sheath flow driver.

Systems according to the invention can help to characterize a variety of different particulate materials in industrial settings, such as in the manufacture of pharmaceuticals. This can help to provide ongoing quality control and quality assurance in the manufacture of such materials.

DETAILED DESCRIPTION OF AN ILLUSTRATIVE EMBODIMENT

Figure 1:
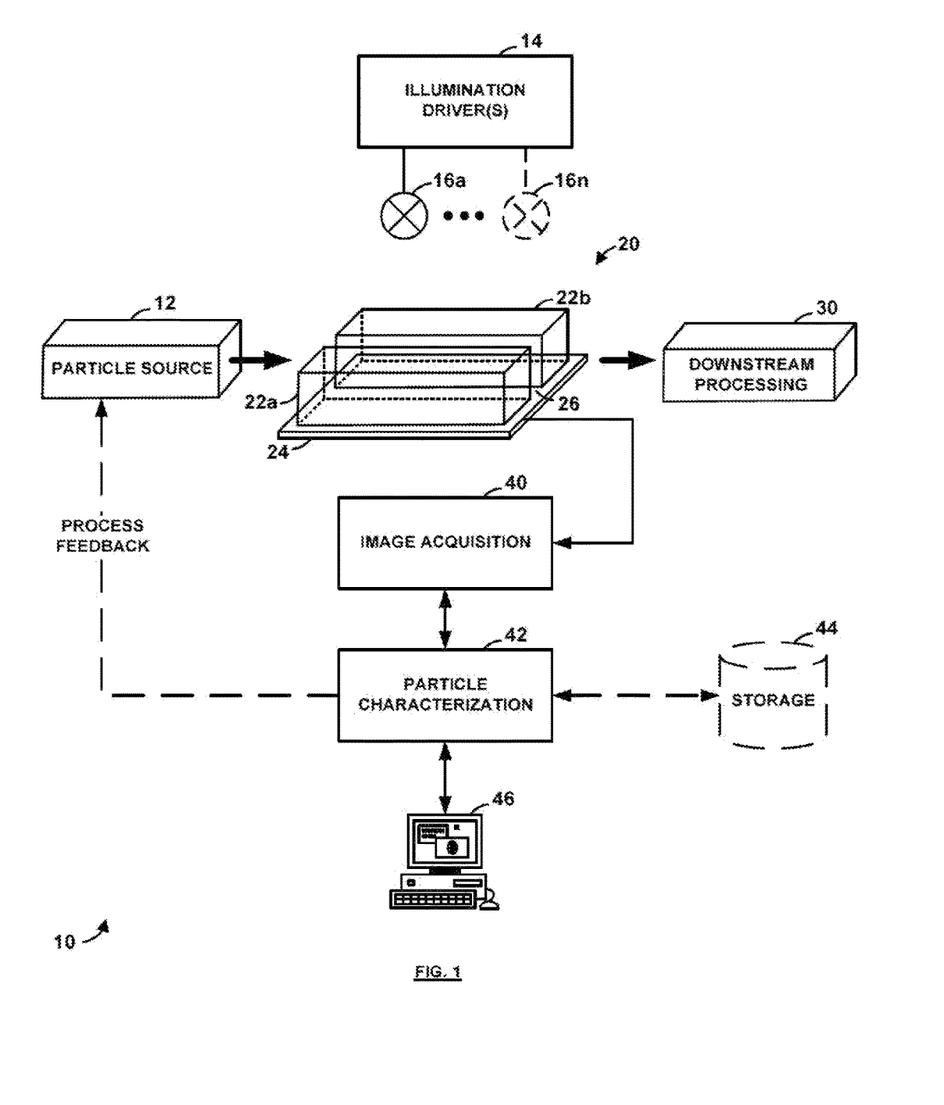
FIG. 1 is a block diagram of a particle characterization system according to the invention.

Referring to FIG. 1, a particle characterization system 10 according to the invention characterizes particles from a particle source 12, such as an industrial process. The process can perform a number of different types of operations on the particles, such as creating them, modifying them, and/or mixing them. In one example, the process is a dispersive process that disperses the active and inactive ingredients of a pharmaceutical agent.

The system 10 also includes one or more illumination drivers 14 that drive one or more illumination sources 16a . . . 16n. These sources can be of a variety of different types and can exhibit a variety of different spectral characteristics. Some examples include visible wavelength illumination sources, narrowband coherent fluorescence excitation sources, or even simple ambient light sources. In a preferred embodiment, the illumination driver includes strobing circuitry that allows short illumination pulses to be produced.

The particle source 12 provides particles that are suspended in a liquid that is passed through a microfluidic detection cell 20. The cell 20 includes a hydraulic channel 26 that passes above or alongside a two-dimensional array image detector 24, such as a CCD or CMOS image sensor. This cell can be fabricated using a variety of different techniques, such as by machining a metal block or molding a plastic part to define a channel between a pair of walls 22a, 22b above the detector 24. In one embodiment, the cell 20 is made of glass with a plastic manifold. The suspended particles can be conveyed through the microfluidic system 20 in a variety of known ways, such as by pumping, gravity, or capillary action.

The system 10 can provide images without the use of any lenses and this can improve its performance, reliability, and keep its cost down. A lensless system has a deeper field of view and it can therefore have a higher throughput. It also does not need focus adjustments, and its reduced part count can make it less vulnerable to breakdown. In some embodiments, a lens may be provided between the sample flow in the channel 26 and the detector 24.

Figure 2:
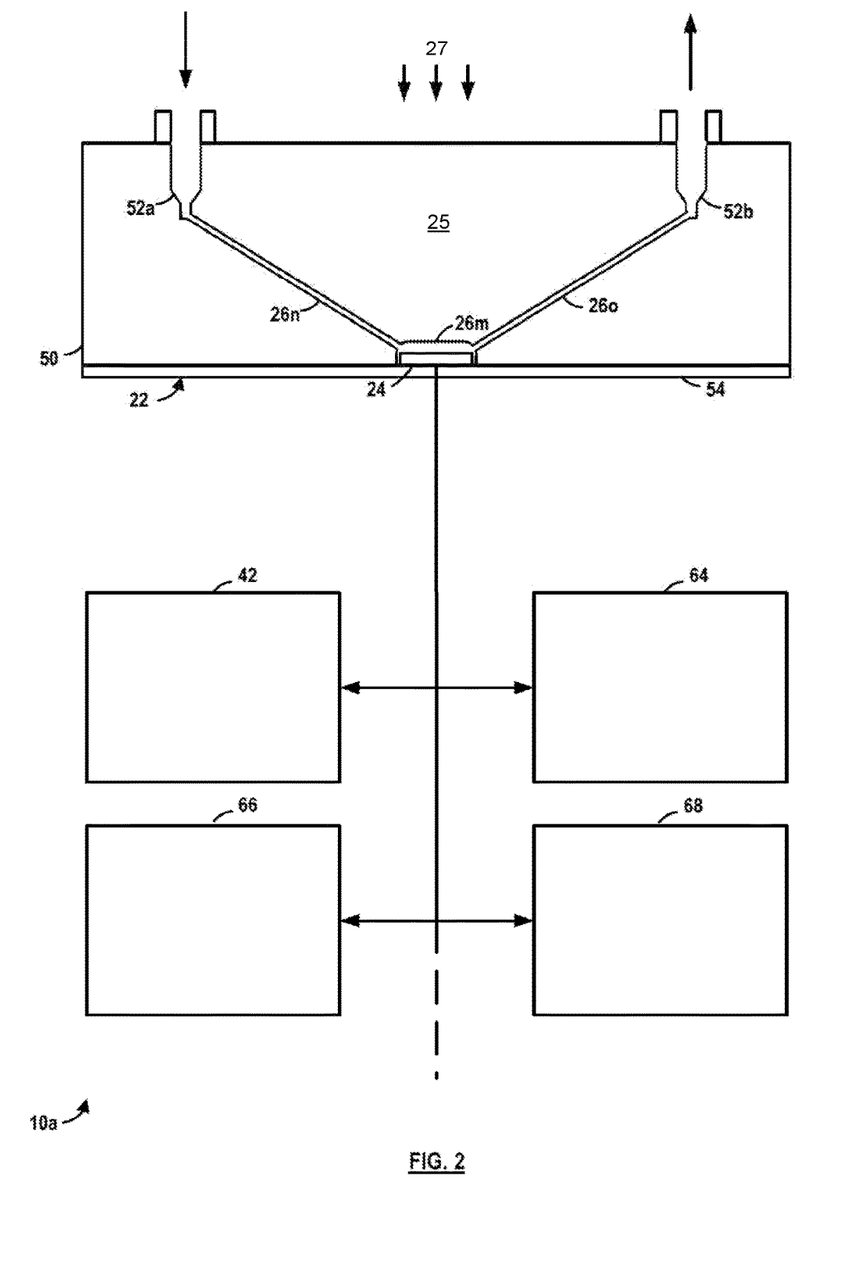
FIG. 2 is a diagram of a microfluidic detection cell according to the invention.

Referring also to FIG. 2, a cell channel block 22 can be built using a clear acrylic block that is placed on top of a circuit board 54 that supports a two-dimensional detector or image sensor 24 opposite an unobstructed or transparent portion 25 of the block 22 through which the detector 24 can be illuminated with light 27 from the light source(s) 16a-16n (FIG. 1). The block 22 is hollowed out to form an imaging chamber 26m, which may also be termed a hydraulic detection channel or a detection channel, around the two-dimensional detector 24, and channels are drilled through the block 22 to form access channel portions 26n, 26o that connect the imaging chamber 26m with hydraulic fittings 52a, 52b. In one embodiment, the imaging chamber 24 is milled out of the block 22 and its inside surface is then polished to eliminate scratches from the milling operation. Cells can also be made of glass to obtain optically clear surfaces.

In a general aspect therefore, the detection cell 20 may comprise a block 22 with inlet and outlet channels 26n, 26o connecting an imaging chamber 26m with hydraulic fittings 52a, 52b, an image sensor 24 being provided along a face of the imaging chamber 26m opposite a transparent portion 25 of the block 22. In use, the imaging chamber 26m is illuminated by light transmitted through the transparent portion 25 of the block 22.

Referring again to FIG. 1, an image acquisition subsystem 40 acquires images from the two-dimensional array detector 24. This subsystem 40 can be synchronized with the illumination driver(s) 14 and light source(s) 16a-n in the case of strobed illumination, allowing for high-speed acquisition of particle images. The acquired images can then be processed through downstream image processing subsystems, such as a particle characterization subsystem 42, a particle counting system 64, a depth correction subsystem 66, and a statistical analysis subsystem (shown in FIG. 2). The particle characterization subsystem 42 allows differently shaped particles to be categorized into a number of defined morphological and/or color categories, as for example described in more detail in PCT published application number WO/2013/190326, the contents of which are incorporated herein by reference. The statistical analysis module 68 can be used to develop statistics about the spatial distribution of particle types in the system.

The particle counting subsystem 64 counts each unique particle that enters the imaging chamber 26m to provide an overall particle count over a particular interval. The interval length can encompass all of the particles in a dispersed sample or one or more subsets of that sample. In one embodiment, the particle counting subsystem 64 increments the particle count as each particle first appears on one of the images. Combined operation of the particle characterization and counting subsystems 42, 64 allows counts of different kinds of particles, such as differently sized, shaped, and/or colored particles, to be tallied separately. In this embodiment, the channels 26n, 26o are configured such that all particles pass in front of the detector 24, although bypass channels (not shown) can also be used such that only a subset of particles are detected, as described for example in more detail in PCT published application number WO/2013/190326. For the counting to take place reliably, the hydraulic system, i.e. the cell channel block 22, is preferably designed to produce fully-developed laminar flow through the detection chamber 26m. This allows predictable tracking between images and therefore helps to avoid overcounting.

Figure 3:
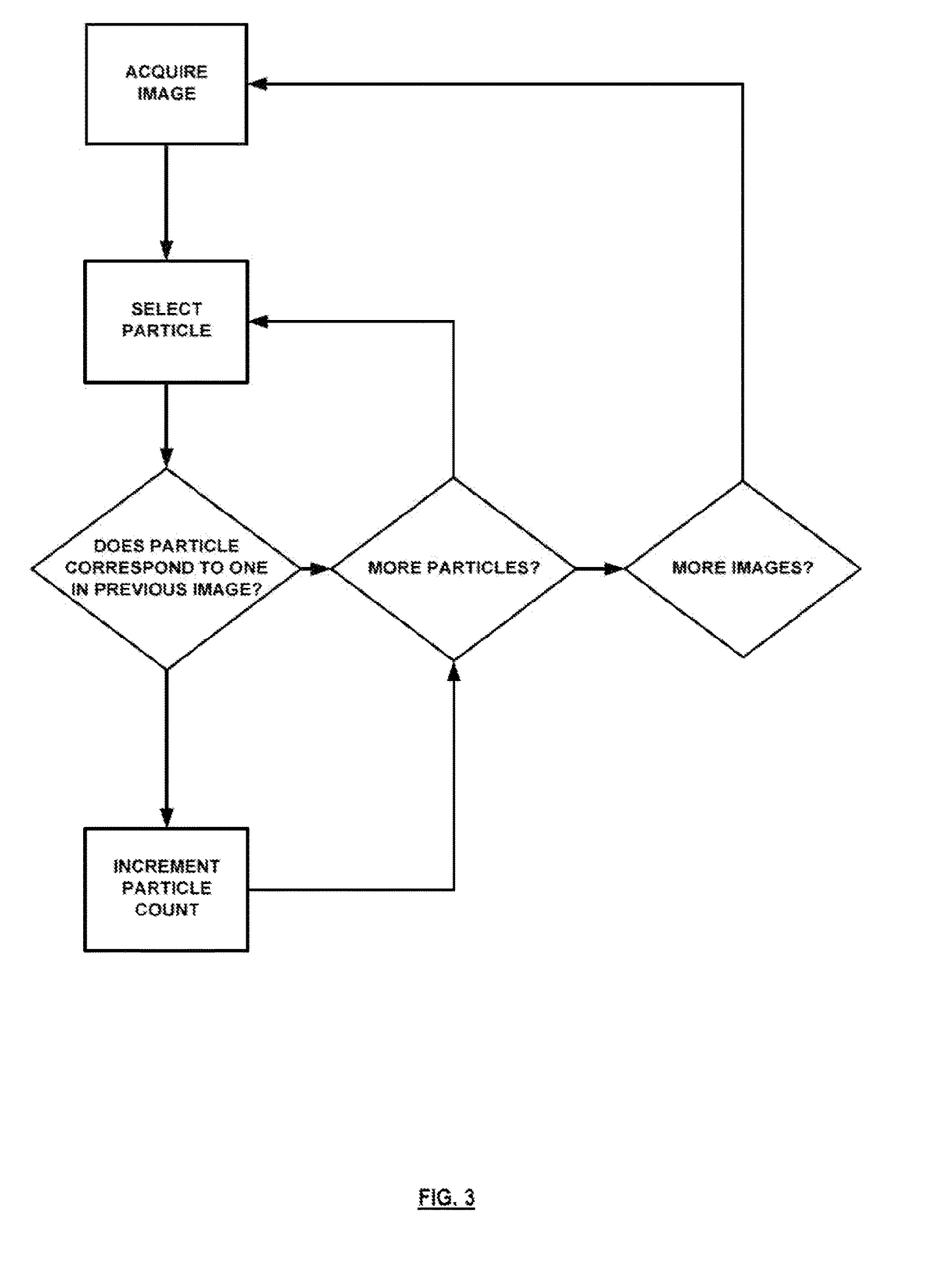
FIG. 3 is a flowchart illustrating counting operations for the microfluidic detection cell of FIG. 2.

Referring to FIG. 3, the particle counting subsystem 64 operates by determining whether each particle in a frame corresponds to one in an earlier frame. If it does not, it is treated as a new particle and counted. If not, it is not counted. This process is repeated for successively acquired frames and the count at the end of the last frame is the total count for the sample. This counting method allows the frame rate to be set to be slightly shorter than the transit time for the fastest particles, which generally occur at the center of the channel.

In a general aspect therefore, a time period between acquisition of successive images from the image sensor 24 is set to be shorter than a shortest transit time of particles flowing through the cell channel block 22 past the image sensor 24.

Different criteria can be used to determine whether a particle corresponds to one in an earlier frame. One simple approach is to look for particles detected at the same position across the channel (corresponding to a y axis orthogonal to the flow direction past, and in the plane of, the image sensor 24). Another approach is to check that the particle is moving with the flow in the right direction, and possibly by the right amount (with movement along an x axis aligned with the flow direction past the image sensor 24 either increasing or within a predetermined range). Shape, size, and other features of the particle can also be taken into consideration. In one embodiment, particles are first tested for their position and then particle shape and size are used as a second test if the positions correspond.

In a general aspect therefore, particles detected in first and second successive images may be determined to be the same particle, and therefore counted only once, according to one or both of the following tests: i) if a position of a particle along a first axis orthogonal to the flow direction in the second image is within a predetermined range around a position of a particle along the first axis in the first image; ii) if a position of a particle in the second image along a second axis parallel to the flow direction is within a predetermined range around a position offset along the second axis from a position of a particle in the first image, the offset being dependent on a fluid flow velocity through the cell channel block 22 past the image sensor 24.

The depth correction subsystem 66 helps to determine how far individual particles are from the surface of the two-dimensional array detector or image sensor 24. Its output can then be used to correct for differences in apparent sizes of particles at different depths. The depth correction subsystem can operate in a variety of ways, such as by examining the particles for blurring at the edges, and/or by using the speed of particles to assign them to layers of fluid at different distances from the detector, which tend to move at different speeds in the case of laminar flow. Particles of known size can also be used as indicators of depth. Another approach is to illuminate the particles with differently colored sources (e.g., RGB matched to corresponding Bayer filter characteristics on the detector chip) and then looking at where the corresponding images fall with respect to each other. Knowing the depth of particles and/or otherwise tracking the particles from frame to frame can help to reduce counting errors, such as may be introduced by noise, differential particle velocities, and interactions with flow cell walls. Where color is used to detect depth, the differently colored sources can be pulsed at the same rate, so there is no loss of throughput.

Operations can be performed by these subsystems 42, 64, 66, 68 in any order and/or in parallel. For example, the particle characterization subsystem 42 can first characterize the particles in the images and store the results, with the particle counting subsystem 64 then counting the differently characterized particles.

Figure 4:
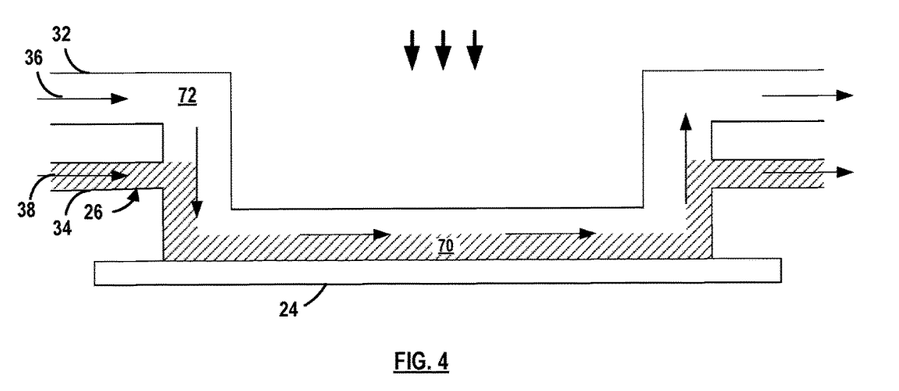
FIG. 4 is a diagrammatic cross section of a flow-focusing microfluidic detection cell according to the invention.

Referring to FIG. 4, a microfluidic detection cell 26 can employ flow focusing to position the particles closer to the two-dimensional array detector 24, such as through the use of one-sided sheath flow. In this approach, a suspended particulate sample flows through a volume 70 that is adjacent to the two-dimensional array detector 24, and a flow of sheath fluid 72, which may or may not be the same fluid in which the particles are suspended, flows above or alongside the sample fluid at a higher flow rate. The elution resulting from the combined flows can then be split to recover the sample back at high concentration. Flow focusing allows smaller particles to be detected in larger channels by reducing diffraction effects. This allows for improved imaging of small particles while simultaneously allowing imaging of larger particles up to the full depth of the channel. It is noted that in the present embodiment, there is no discontinuity in the overall laminar flow profile, even though the sheath flow may be much faster than the sample flow.

Figure 5:
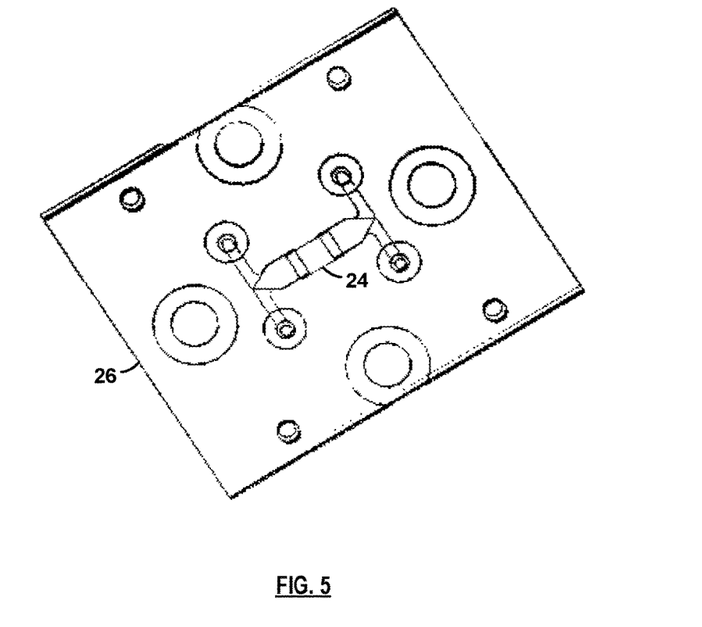
FIG. 5 is a plan view of an implementation of the flow-focusing microfluidic detection cell of FIG. 4.
Figure 6:
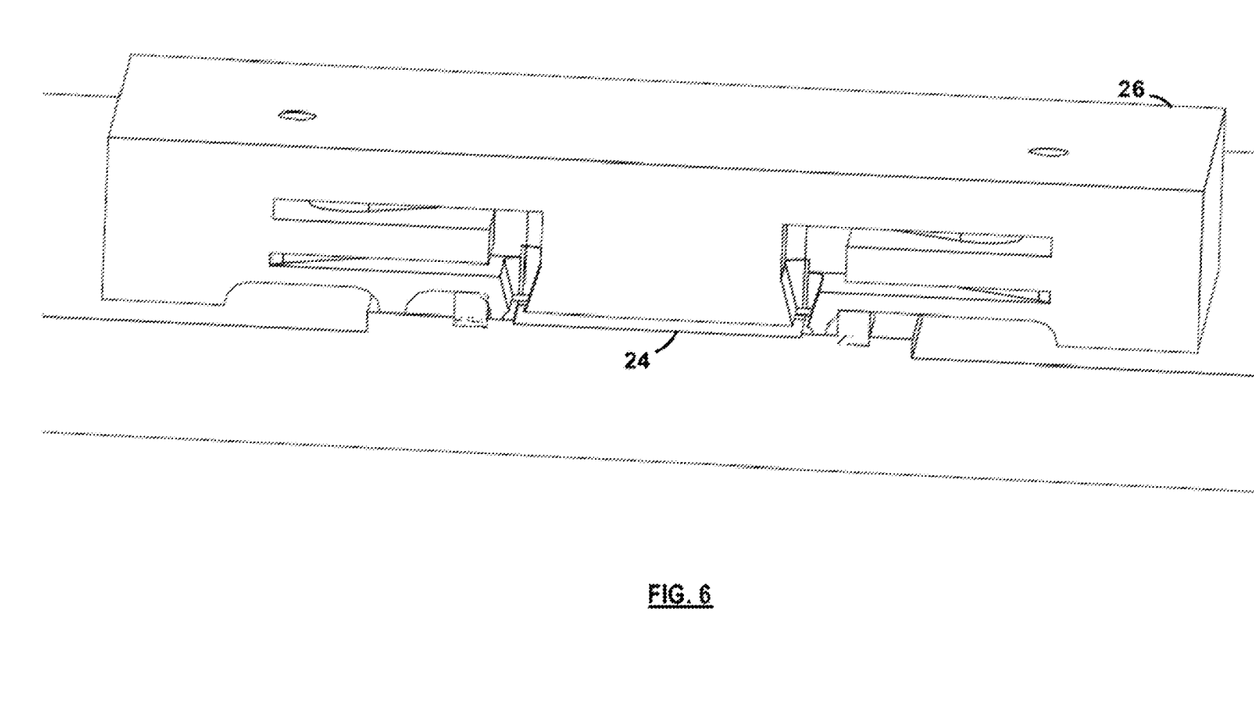
FIG. 6 is a cross-section of another implementation of the flow-focusing microfluidic detection cell of FIG. 4.

As shown in FIG. 5, this type of detector can be implemented using an acrylic block in which the sample and sheath flow from the top of an acrylic block mounted on a circuit board that holds the two-dimensional array detector 24. FIG. 6 shows the channel shapes for another implementation of a microfluidic sheath-flow cell. A gasket is used to create a seal between the two-dimensional array detector and the channel block.

In a general aspect therefore, as with the embodiment in FIG. 2 the detection cell 20 may comprise a block 22 with first inlet and outlet channels connecting an imaging chamber with respective first and second hydraulic fittings, an image sensor 24 being provided along a face of the imaging chamber opposite a transparent portion of the block. In the embodiment in FIG. 4, second inlet and outlet channels are also provided, which connect the imaging chamber 26m with respective third and fourth hydraulic fittings. In use, a sample fluid with suspended particles to be imaged by the image sensor 24 is flowed through the first inlet channel, and a sheath fluid is flowed through the second inlet channel.

Systems according to the invention can be applied to a number of different types of processes, such as Metals, Mining, and Minerals (MMM) applications or the manufacture of pharmaceuticals, personal care products, foodstuffs, pigments, and biomaterials.

Example 1

A flow-focusing microfluidic detection cell was built generally in accordance with FIGS. 1, 4 and 5 using a 5-megapixel iPhone® camera chip. A suspension was made up of a mixture of 3.2 μm and 5 μm polystyrene microspheres in water. This suspension was pumped through the channel using a syringe pump. Flow focusing allowed smaller particles to be brought to within 10 μm of the detector in a 100-μm-deep channel.

The suspension was illuminated with a strobed, white-light LED with a strobe pulse length of about 72 ms. Instead of using the chip's built-in shuttering capabilities, its sensor was left in acquisition mode and strobe pulses were used to define the acquisition period. The particles were sized and counted.

Figure 7A:
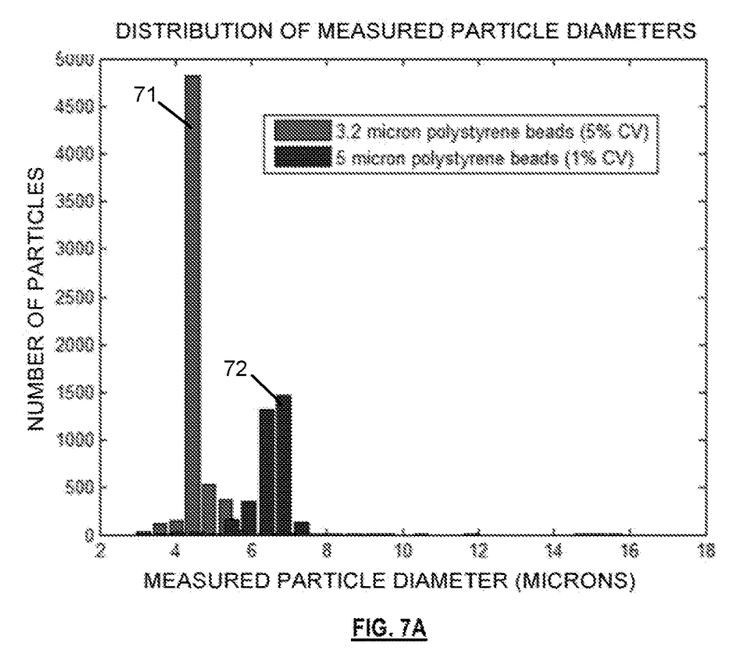
FIG. 7A is a first plot of measured particle diameters using an implementation of the flow-focusing microfluidic detection cell of FIG. 4.

Results for the experiment are shown in FIG. 7A. This figure shows two distinct peaks 71, 72 for the two sizes of particles, the first peak 71 corresponding to the 3.2 μm beads and the second peak 72 corresponding to the 5 μm beads. This ability to resolve particle sizes below 10 μm is particularly useful in identifying particulate matter such as protein aggregates, silicone oil droplets, glass, rubber and metal, for example to help diagnose sources of contamination in protein formulations.

Example 2

Another implementation of the focusing microfluidic detection cell was built generally in accordance with FIGS. 1, 4 and 5 using a 5-megapixel iPhone® camera chip. In this embodiment, the Ansys CFX software package available from Ansys Inc. was used to optimize the flow during the design process. A suspension was then made up of a mixture of 1, 2, 3, 4, and 5 micro polystyrene microspheres in water. This suspension was pumped through the channel using a syringe pump, and the particles were sized and counted.

Figure 7B:
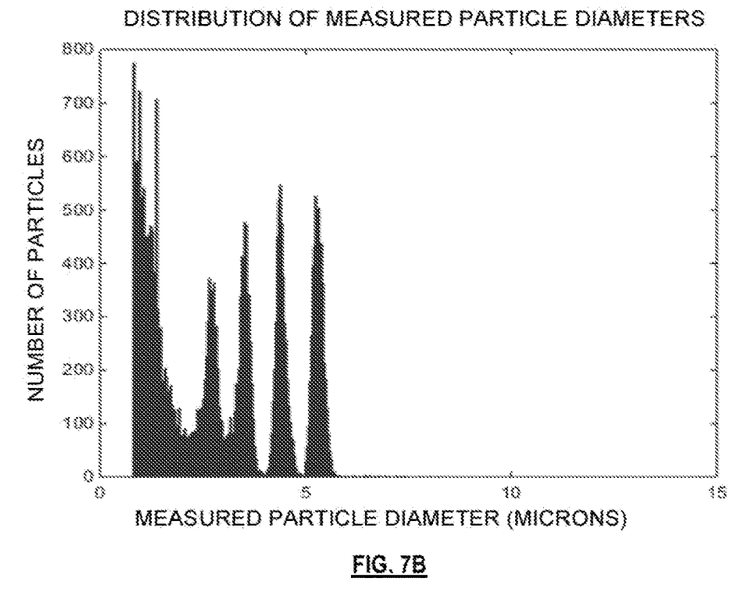
FIG. 7B is a second plot of measured particle diameters using another implementation of the flow-focusing microfluidic detection cell of FIG. 4.

Results for the experiment are shown in FIG. 7B. This figure shows distinct peaks for all five sizes of particles.

Overall, providing a lensless, flow-focused design with a channel width of about 100 μm has proven to be highly versatile in a variety of pharmaceutical and protein research tasks. It can accommodate and image larger particles that might otherwise clog the system while allowing particles smaller than 10 μm to be imaged and characterized. Particles as small as 1 μm are readily distinguishable from larger ones and it is contemplated that even smaller particles, such as particles on the order of 0.5 μm could also be characterized. In a general aspect therefore, the imaging chamber of the detection cell may have a width in a direction normal to the plane of the image sensor of between 50 and 150 μm, optionally between 80 and 120 μm and preferably around 100 μm. The particle characterization system may be capable of resolving and counting individual particles having a size of less than 10 μm and optionally greater than 1 μm or 0.5 μm.

Figure 8:
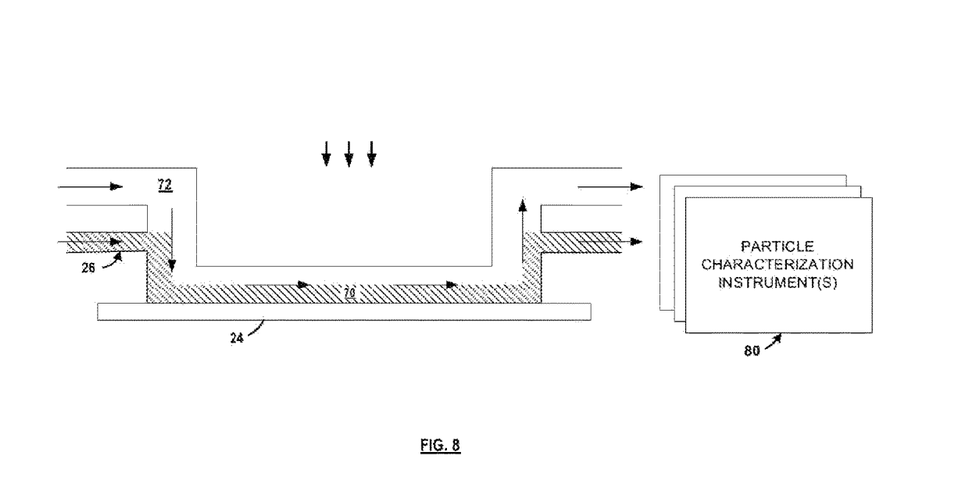
FIG. 8 is a diagrammatic cross section of a flow-focusing and flow-separating microfluidic detection cell according to the invention.

Referring to FIG. 8, the flow-focusing principles discussed above can also be applied to separate smaller particles for other types of measurements. For example, the portion of the sample flowing through the flow-focused volume 70 could be recovered and introduced into one or more downstream particle characterization instruments 80, such as a Dynamic Light Scattering (DLS)-, Resonant Mass Measurement (RMM)-, and/or Nanoparticle Tracking Analysis (NTA)-based particle characterization instrument. The separation of smaller particles from larger particles is particularly useful in a DLS measurement in which signals from larger particles can swamp out signals from smaller particles. Separating out smaller particles can also prevent clogging by larger particles in some instrument configurations.

Measurements can be performed on the separated small-particle sample fraction as it flows out of the detection cell 20 or after collection in a test cuvette. In some embodiments, the large particles that were separated out of the sample can be recombined with the smaller particles, possibly after separate testing, to recover the sample. While the flow-focusing separation is shown in connection with the imaging of the sample, it could also be performed before or after the imaging step or even independent of any imaging of the sample. In one example, the flow focusing stream is a 10 μm portion that is separated from a 90 μm sheath.

A suitable DLS instrument for use in this type of system includes the Zetasizer particle measurement system. A suitable RMM instrument is the Archimedes particle metrology system. And a suitable NTA instrument is the Nanosight nanoparticle characterization system. All of these instruments are available from Malvern Instruments Limited, of Malvern, UK. Results from these instruments can be used separately or they can be combined and/or contrasted with results from the imaging cell.

Figure 9:
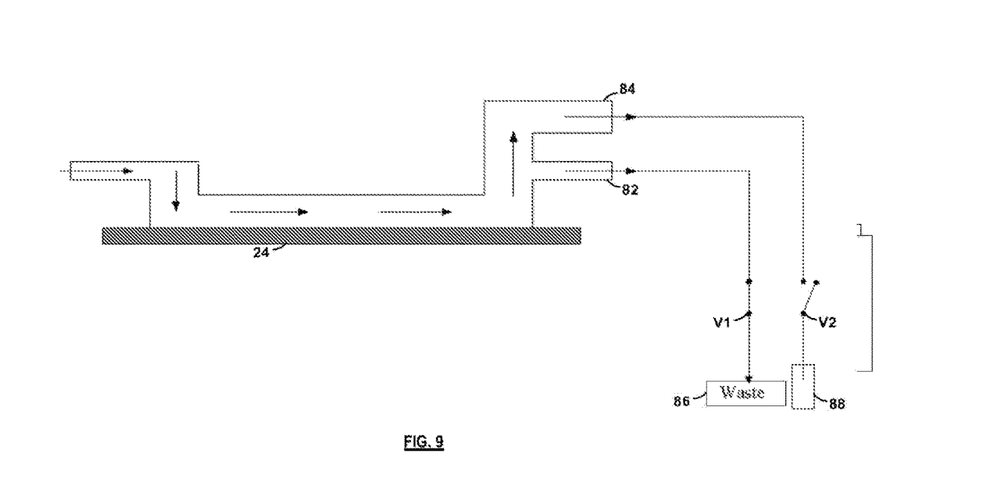
FIG. 9 is a diagrammatic cross section of a microfluidic detection cell with particle output selection.

Referring to FIG. 9, particle characterization systems according to the invention can also be equipped with particle sorting to allow concentration and/or isolation of particular particles. The sorted particles can then be collected and/or sent to one or more of the downstream particle characterization instruments 80 (FIG. 8). Particles can be sorted based on any detected characteristic, such as size, shape, or refractive index. In one embodiment, illustrated in FIG. 9, particle sorting is implemented with two on-off switching valves V1, V2 provided downstream of the detector 24 to switch between a sample out (or first) conduit 82 that leads to a waste container 86 and a sorted/enriched sample out (or second) conduit 84 that leads to a sorted/enriched sample vial 88, although the system could also be configured to sort particles among a larger number of destinations. This type of embodiment can be particularly helpful in analyzing different types of contaminant particles found in pharmaceutical preparations.

In a general aspect therefore, as with the embodiment in FIG. 2 the detection cell 20 may comprise a block 22 with first inlet and outlet channels connecting an imaging chamber with respective first and second hydraulic fittings, an image sensor 24 being provided along a face of the imaging chamber opposite a transparent portion of the block. In the embodiment in FIG. 9, a second outlet channel is also provided, which connects the imaging chamber 26m with a third hydraulic fitting. The first and second outlet channels are connected to first and second collection points 86, 88 via first and second switchable valves V1, V2. In use, the valves V1, V2 are operated to selectively direct fluid flowing from the imaging chamber to the collection points 86, 88.

Figure 10:
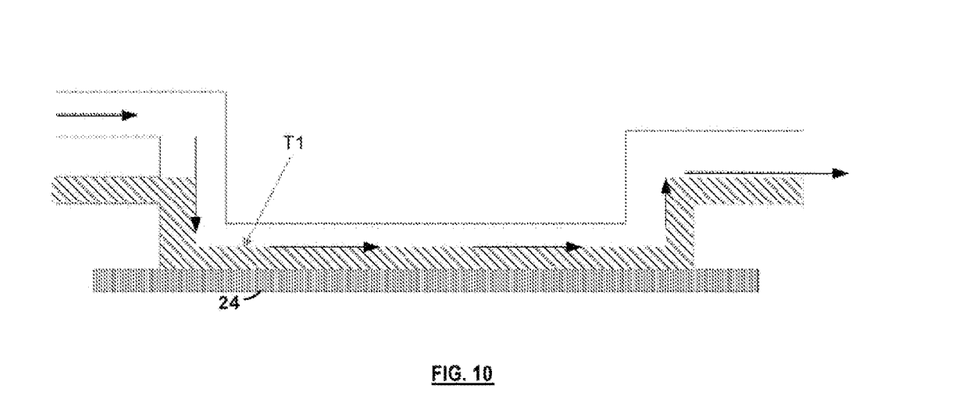
FIG. 10 is a diagrammatic cross section of a variable flow-focusing microfluidic detection cell according to the invention set at a first flow-focusing ratio.
Figure 11:
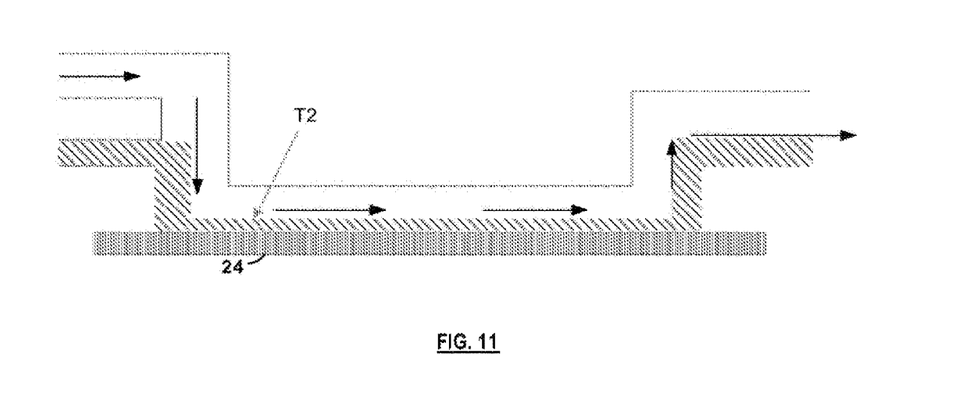
FIG. 11 is a diagrammatic cross section of the variable flow-focusing microfluidic detection cell of FIG. 10 set at a second flow-focusing ratio that is higher than the first flow-focusing ratio presented in FIG. 10.

Referring to FIGS. 10 and 11, a particle characterization system 10 according to the invention can also employ variable flow-focusing. This can be accomplished by varying a ratio (termed the flow focusing ratio) between the flow rates of the sheath fluid and sample fluid, such as by controlling the relative speed of the pumps that provide these flows. Where the sheathing rate is lower (FIG. 10), the sample fluid will exhibit a higher thickness t1 and where the sheathing rate is higher (FIG. 11), the sample fluid will exhibit a lower thickness t2. The flow focusing ratio can be set through the system's software to allow the user to select a thickness suitable for a particular experiment. Generally, lower thicknesses should provide better imaging at the expense of a lower throughput, and vice-versa. Variable flow focusing can be provided in both single-output and multi-output systems.

With a flow focusing ratio (sheath to sample) of 12.5, the sample fluid is squeezed within 16.6 µm from the sensor, which allows particles equal to or greater than 3 µm to be imaged with high resolution on the lensless system. With a flow focusing ratio (sheath to sample) of 50, the sample fluid is squeezed within 8.3 µm from the sensor, which allows particles equal to or greater than 2 µm to be imaged with high resolution. The interface between sample and sheath is soft and so large particles can still go through the 100 µm flow cell depth. Variable flow focusing on a lensless system therefore allows its dynamic range to be adjusted.

In a general aspect therefore, a flow rate of the sheath fluid is controlled to control a thickness of the sample fluid flowing past the image sensor 24, a higher flow rate of sheath fluid corresponding to a lower thickness of the sample fluid. A ratio between the flow rate of the sheath fluid to the flow rate of the sample fluid may for example be between 10 and 50.

Particle characterization systems according to the invention can also be pumped in reverse to recover the undiluted sample. In this case, both the sample fluid and sheath fluid are pumped in reverse, and should remain unmixed during this operation (assuming laminar flow is maintained). This may require an extended holding conduit downstream of the imaging cell whose length will depend on the volume of the sample fluid to be recovered. The flow can be reversed in different ways, such as by reversing sample and sheath flow pumps or through the use of selector valves.

Operations on the images as well as control operations, including control of the drivers, can be performed in connection with special-purpose software programs running on general-purpose computer platforms in which stored program instructions are executed on a processor, but they could also be implemented in whole or in part using special-purpose hardware. While the system can be broken into the series of modules and steps shown for illustration purposes, one of ordinary skill in the art would recognize that it is also possible to combine them and/or split them differently to achieve a different breakdown.

The present invention has now been described in connection with a number of specific embodiments thereof. However, numerous modifications which are contemplated as falling within the scope of the present invention should now be apparent to those skilled in the art. For example, while the particles are described as being suspended in a liquid in the embodiments shown, they can also be suspended in a gas. More comprehensively, systems according to the invention are or may be applicable to colloids in general, i.e. heterogeneous fluid samples that include a continuous liquid or gas phase and a discontinuous phase that can include either a liquid, solid, or gas. It is therefore intended that the scope of the present invention be limited only by the scope of the claims appended hereto. In addition, the order of presentation of the claims should not be construed to limit the scope of any particular term in the claims.

The invention claimed is:

1. A particle characterization method, comprising:
providing a fluid containing suspended particles;
causing at least a first subset of the suspended particles to flow past a first two-dimensional array detector;
causing a sheath flow to flow adjacent the flow caused by the step of causing the suspended particles to flow, to direct the flow of suspended particles toward the two-dimensional array detector;
illuminating the first subset of suspended particles as they flow past the first two-dimensional array detector in the fluid;
acquiring a plurality of images of the first subset of particles as they flow past the first two-dimensional array detector in the fluid.

2. The method of claim 1 wherein the steps of causing flow cause a laminar flow.

3. The method of claim 1 further including the step of recovering the suspended particles in a higher concentration by splitting an elution resulting from a combination of the particle flow and the sheath flow.

4. The method of claim 1 wherein the method is performed independent of any lens.

5. The method of claim 1 further including the step of reversing both the particle flow and the sheath flow to recover the particles.

6. The method of claim 1 further including the step of adjusting a ratio between a rate of flow of the particle flow and a rate of flow of the sheath flow to vary the thickness of the particle flow.

7. The method of claim 6 wherein the ratio is between 10 and 50.

8. A particle characterization instrument, comprising:
a hydraulic detection channel having first and second opposing faces;
a lensless two-dimensional array detector provided along the first face of the hydraulic detection channel and having a field of view across the hydraulic detection channel;
a sample fluid channel opening into the hydraulic detection channel and positioned to direct a sample flow across the first face of the hydraulic detection channel within the field of view of the array detector;
a sheath fluid channel opening into the hydraulic detection channel and positioned to direct a sheath flow adjacent the sample flow across the second face of the hydraulic detection channel, wherein the sheath fluid channel is configured to direct the sheath flow above the sample fluid, thereby positioning the sample flow closer to the two-dimensional array detector; and an illumination source positioned to illuminate the sample flow within the field of view of the array detector.

9. The particle characterization instrument of claim 8 further including a sample flow driver hydraulically connected to the sample flow channel, a sheath flow driver hydraulically connected to the sheath flow channel, and means for adjusting a ratio between a flow rate of the sample flow driver and a flow rate of the sheath flow driver.

10. The instrument of claim 8 wherein hydraulic detection channel has a width in a direction normal to the plane of the detector of between 50 and 150 μm.

11. The instrument of claim 8 wherein hydraulic detection channel has a width in a direction normal to the plane of the detector of between 80 and 120 μm.

12. The instrument of claim 8 wherein hydraulic detection channel has a width in a direction normal to the plane of the detector of around 100 μm.

13. The particle characterization instrument of claim 8 further comprising a sample outlet channel, for recovering the sample fluid after the sample fluid has flowed past the two-dimensional array detector, and a sheath fluid outlet channel for receiving a flow of sheath fluid after the sheath fluid has flowed past the two-dimensional array detector.

14. The method of claim 1 wherein the sheath flow is a one-sided sheath flow.

15. The method of claim 1 wherein a channel through which the suspended particles and the sheath flows past the first two-dimensional detector forms an imaging chamber having a width in a direction normal to the plane of the detector of between 50 and 150 μm.

16. The method of claim 1 wherein a channel through which the suspended particles and the sheath flows past the first two-dimensional detector forms an imaging chamber having a width in a direction normal to the plane of the detector of between 80 and 120 μm.

17. The method of claim 1 wherein a channel through which the suspended particles and the sheath flows past the first two-dimensional detector forms an imaging chamber having a width in a direction normal to the plane of the detector of around 100 μm.

18. The method of claim 1 further comprising automatically counting the particles in the images.

* * * * *